(12) United States Patent
Botzer et al.

(10) Patent No.: US 10,993,659 B2
(45) Date of Patent: May 4, 2021

(54) AUTOMATIC DETECTION OF PHRENIC NERVE STIMULATION

(71) Applicant: Biosense Webster (Israel) Ltd., Yokneam (IL)

(72) Inventors: Lior Botzer, Timrat (IL); Daniel Osadchy, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 269 days.

(21) Appl. No.: 15/610,994

(22) Filed: Jun. 1, 2017

(65) Prior Publication Data

US 2018/0344244 A1 Dec. 6, 2018

(51) Int. Cl.
*A61B 5/05* (2021.01)
*A61B 5/00* (2006.01)
*A61B 5/0538* (2021.01)
*A61B 18/14* (2006.01)
*A61B 5/08* (2006.01)
*A61B 18/12* (2006.01)
(Continued)

(52) U.S. Cl.
CPC ......... *A61B 5/4893* (2013.01); *A61B 5/0538* (2013.01); *A61B 5/0809* (2013.01); *A61B 5/24* (2021.01); *A61B 5/6852* (2013.01); *A61B 5/746* (2013.01); *A61B 18/1233* (2013.01); *A61B 18/1492* (2013.01); *A61B 5/063* (2013.01); *A61B 5/296* (2021.01); *A61B 34/20* (2016.02); *A61B 90/37* (2016.02); *A61B 2018/00577* (2013.01); *A61B 2018/00839* (2013.01); *A61B 2018/00898* (2013.01); *A61B 2034/2053* (2016.02)

(58) Field of Classification Search
CPC ..... A61B 5/4893; A61B 5/746; A61B 5/0809; A61B 5/0538; A61B 5/04001; A61B 5/6852; A61B 5/063; A61B 5/0492; A61B 18/1492; A61B 18/1233; A61B 2018/00577; A61B 2018/00839; A61B 2018/00898; A61B 34/20; A61B 90/37; A61B 2034/2053; A61B 5/1107; A61B 5/4052; A61B 5/686
See application file for complete search history.

(56) References Cited

U.S. PATENT DOCUMENTS 6,772,008 B2    8/2004   Zhu
7,299,093 B2   11/2007   Zhu
(Continued)

OTHER PUBLICATIONS

Extended European Search Report for corresponding European patent application No. EP 18175358.3, dated Oct. 23, 2018.

*Primary Examiner* — Navin Natnithithadha
*Assistant Examiner* — Andrey Shostak (57) ABSTRACT

Described embodiments include an apparatus, including a display and a processor. The processor is configured to navigate a catheter to a particular location within a body of a subject, using each one of a plurality of electrodes coupled to the body of the subject. The processor is further configured to identify, subsequently, from a signal that represents an impedance between a given pair of the electrodes, that a phrenic nerve of the subject was stimulated by a pacing current passed from the catheter into tissue of the subject at the particular location, and to generate an output on the display, in response to the identifying. Other embodiments are also described.

18 Claims, 2 Drawing Sheets

(51) Int. Cl.
*A61B 5/24* (2021.01)
*A61B 18/00* (2006.01)
*A61B 90/00* (2016.01)
*A61B 34/20* (2016.01)
*A61B 5/06* (2006.01)
*A61B 5/296* (2021.01)

(56) References Cited

U.S. PATENT DOCUMENTS

| | | | |
|---|---|---|---|
| 8,260,421 | B2 | 9/2012 | Sathaye |
| 8,456,182 | B2 | 6/2013 | Bar-Tal |
| 8,532,774 | B1 * | 9/2013 | Hedberg .............. A61B 5/0538 607/18 |
| 8,617,228 | B2 | 12/2013 | Wittenberger |
| 8,996,108 | B2 | 3/2015 | McCabe |
| 9,031,651 | B2 | 5/2015 | Rockweiler |
| 2008/0300644 | A1 * | 12/2008 | Sathaye ............ A61N 1/36521 607/28 |
| 2009/0203992 | A1 * | 8/2009 | Govari ................ A61B 5/0538 600/424 |
| 2009/0210024 | A1 * | 8/2009 | M. ....................... A61B 5/4029 607/28 |
| 2010/0125306 | A1 | 5/2010 | McCabe |
| 2010/0191137 | A1 | 7/2010 | Brada |
| 2010/0241113 | A1 | 9/2010 | Ingle |
| 2010/0305647 | A1 * | 12/2010 | McCabe ............ A61B 5/04001 607/18 |
| 2013/0109994 | A1 | 5/2013 | Cho |
| 2013/0296850 | A1 * | 11/2013 | Olson ................ A61B 18/1492 606/41 |
| 2013/0310829 | A1 | 11/2013 | Cohen |
| 2014/0180278 | A1 | 6/2014 | Abboud et al. |
| 2014/0277280 | A1 | 9/2014 | Saha |
| 2014/0358135 | A1 * | 12/2014 | Sambelashvili ....... A61B 18/02 606/21 |
| 2015/0057563 | A1 * | 2/2015 | Kowalski ........... A61B 5/04001 600/554 |
| 2015/0141798 | A1 | 5/2015 | Bar-Tal |
| 2015/0265840 | A1 * | 9/2015 | Ghosh ................ A61B 5/04001 607/27 |
| 2015/0272664 | A9 | 10/2015 | Cohen |
| 2015/0351660 | A1 * | 12/2015 | An ...................... A61B 5/0538 600/484 |
| 2018/0310978 | A1 * | 11/2018 | Avitall .................... A61B 5/01 |

* cited by examiner

AUTOMATIC DETECTION OF PHRENIC NERVE STIMULATION

FIELD OF THE INVENTION

The present invention relates to the field of medical procedures, especially cardiac ablation procedures.

BACKGROUND

The left and right phrenic nerves, which may be collectively referred to in the singular as "the phrenic nerve," descend from the neck to the diaphragm, passing between the lungs and the heart. The phrenic nerve is involved in the control of respiration.

U.S. Pat. No. 8,260,421 describes methods and devices for reducing phrenic nerve stimulation of cardiac pacing systems involving delivering a pacing pulse to a ventricle of a heart. A transthoracic impedance signal is sensed, and a deviation in the signal resulting from the pacing pulse may be used to determine phrenic nerve stimulation. Methods may further involve detecting the phrenic nerve stimulation from the pacing pulse by delivering two or more pacing pulse to the ventricle of the heart, and determining a temporal relationship. A pacing vector may be selected from the two or more vectors that effects cardiac capture and reduces the phrenic nerve stimulation. A pacing voltage and/or pulse width may be selected that provides cardiac capture and reduces the phrenic nerve stimulation. In other embodiments, a pacing pulse width and a pacing voltage may be selected from a patient's strength-duration curve that effects cardiac capture and reduces the phrenic nerve stimulation.

U.S. Pat. No. 8,617,228 describes a method of treating tissue, including positioning a stimulation device proximate a phrenic nerve; stimulating the phrenic nerve with the stimulation device; measuring a physiological response to the stimulation; defining a threshold physiological response value based at least in part on the measured physiological response; positioning a thermal treatment element proximate to an arrhythmogenic cardiac tissue region; applying a thermal treatment regimen to the cardiac tissue region with the medical device; measuring a physiological parameter during the thermal treatment regimen application; and conveying the measured physiological parameter to a controller, the controller comparing the measured physiological parameter to the defined physiological response value threshold, the controller adjusting the thermal treatment regimen in response to the comparison of the measured physiological parameter to the defined physiological response value threshold.

U.S. Pat. No. 6,772,008 describes a cardiac rhythm management device in which an accelerometer is used to detect diaphragmatic or other skeletal muscle contraction associated with the output of a pacing pulse. Upon detection of diaphragmatic contraction, the device may be configured to automatically adjust the pacing pulse energy and/or pacing configuration.

U.S. Pat. No. 8,996,108 describes an implantable cardiac device that includes a sensor for sensing patient activity and detecting phrenic nerve activation. A first filter channel attenuates first frequencies of the sensor signal to produce a first filtered output. A second filter channel attenuates second frequencies of the accelerometer signal to produce a second filtered output. Patient activity is evaluated using the first filtered output and phrenic nerve activation caused by cardiac pacing is detected using the second filtered output.

US Patent Application Publication 2013/0109994 describes systems and methods for monitoring phrenic nerve function of a patient, including establishing a diaphragmatic movement value threshold; positioning a diaphragmatic movement sensor on an external surface of an abdomen of the patient; applying a treatment regimen to a tissue region in proximity to the phrenic nerve; measuring a diaphragmatic movement value with the diaphragmatic movement sensor; comparing the measured diaphragmatic movement value to the established diaphragmatic movement value threshold; and generating an alert in response to the comparison.

US Patent Application Publication 2015/0057563 describes a method and system for monitoring phrenic nerve function and preventing phrenic nerve injury during cardiac ablation. The system includes a pacing device operable to transmit stimulation energy to the phrenic nerve through target tissue proximate the phrenic nerve, and a plurality of assessment electrodes operable to make comparisons between baseline, real-time, and predetermined threshold values for CMAP signal amplitude and amplitude over time. The processing device may be connected to an ablation console, and the processing device may interrupt or adjust an ablation procedure controlled by the ablation console and/or generate a system alert in response to one of these comparisons, if the comparison indicates phrenic nerve injury. The method includes applying stimulation energy to the phrenic nerve, recording diaphragmatic CMAP signals in response to the stimulation energy, and adjusting an ablation procedure and/or automatically generating a system alert in response to comparisons performed by the processing device.

U.S. Pat. No. 9,031,651 describes a system that includes a cardiac pulse generator configured to generate cardiac paces to pace the heart, a sensor configured to sense a physiological signal for use in detecting pace-induced phrenic nerve stimulation where the pace-induced phrenic nerve stimulation is phrenic nerve stimulation induced by electrical cardiac pace signals, and a phrenic nerve stimulation detector configured to analyze the sensed physiological signal to detect PS beats where the PS beats are cardiac paces that induce phrenic nerve stimulation. The detector may be configured to correlate signal data for sensed beat signals to a PS template to detect PS beats, or may be configured to analyze morphological features of sensed beat signals to detect PS beats, or may be configured to detect PS beats using a combination that both correlates signal data for sensed beat signals to a PS template and analyzes morphological features of sensed beat signals.

US Patent Application Publication 2010/0241113 describes a cryotherapy delivery system that includes a cryotherapy catheter having a distal treatment component that delivers, during a cryotherapy procedure, cryotherapy to a treatment site inside a patient's body; a controller that controls the delivery of the cryotherapy during the cryotherapy procedure; and a sensor that measures values of a respiration parameter of the patient during the cryotherapy procedure, and provides measured values to the controller. The controller can determine, prior to delivery of cryotherapy, a baseline value for the respiration parameter; detect, during delivery of the cryotherapy, a change in the respiration parameter relative to the baseline value; and suspend delivery of the cryotherapy when the change exceeds a threshold.

U.S. Pat. No. 8,456,182 describes a method that includes positioning body-electrodes in galvanic contact with a body of a patient and positioning a mapping-tool, having a mapping-electrode, in a plurality of regions in the body. The method further includes tracking the mapping-tool at different positions in each of the regions using a location-measuring system, and for each region, generating a respective set of calibration-currents between the body-electrodes and the mapping-electrode at the different positions in the region. A respective relation is derived for each region between the respective set of the calibration-currents and the different positions, and is used in determining the location of an investigation-tool in response to the different respective relations and investigation-tool-currents.

SUMMARY OF THE INVENTION

There is provided, in accordance with some embodiments of the present invention, apparatus including a display and a processor. The processor is configured to navigate a catheter to a particular location within a body of a subject, using each one of a plurality of electrodes coupled to the body of the subject. The processor is further configured to identify, subsequently, from a signal that represents an impedance between a given pair of the electrodes, that a phrenic nerve of the subject was stimulated by a pacing current passed from the catheter into tissue of the subject at the particular location, and to generate an output on the display, in response to the identifying.

In some embodiments, the processor is further configured to acquire the signal by causing an electric current to be passed between the given pair of the electrodes at least while the pacing current is passed into the tissue.

In some embodiments, the processor is configured to acquire the signal by:

causing respective electric currents to be passed between a plurality of pairs of the electrodes, including the given pair of the electrodes, at least while the pacing current is passed into the tissue, and deriving the signal from respective impedances measured between the pairs of the electrodes while the electric currents are passed.

In some embodiments, the output includes a warning indicating that the tissue at the particular location should not be ablated.

In some embodiments, some of the electrodes are coupled to a front of the subject and some of the electrodes are coupled to a back of the subject, and the pair of the electrodes includes one of the electrodes coupled to the front of the subject and one of the electrodes coupled to the back of the subject.

In some embodiments, the processor is configured to navigate the catheter by repeatedly:

ascertaining a location of the catheter, responsively to different respective impedances exhibited between the catheter and each of the electrodes, and generating an output that indicates the ascertained location.

In some embodiments, the processor is configured to identify that the phrenic nerve of the subject was stimulated by identifying a quivering pattern in at least one portion of the signal.

In some embodiments, the processor is configured to identify the quivering pattern by identifying a longer amount of time between successive zero-crossings of the portion of the signal, relative to other portions of the signal.

In some embodiments, the processor is configured to identify the quivering pattern by identifying a larger amplitude of peaks of the portion of the signal, relative to other portions of the signal.

In some embodiments, the processor is configured to identify that the phrenic nerve was stimulated by identifying that a frequency of the quivering pattern corresponds to a frequency at which the pacing current was passed into the tissue.

In some embodiments, the pacing current is passed into the tissue during a plurality of time periods and with a plurality of different respective pacing frequencies, and the processor is configured to identify that the phrenic nerve was stimulated by identifying that the frequency of the quivering pattern, during each time period of the time periods, corresponds to the pacing frequency with which the pacing current was passed into the tissue during the time period.

In some embodiments, the pacing current is passed into the tissue during a plurality of time periods, and the processor is configured to identify that the phrenic nerve was stimulated by identifying the quivering pattern in those portions of the signal corresponding to the time periods, but not in other portions of the signal.

There is further provided, in accordance with some embodiments of the present invention, a method that includes, using each one of a plurality of electrodes coupled to a body of a subject, navigating a catheter to a particular location within the body of the subject. The method further includes, subsequently, identifying, from a signal that represents an impedance between a given pair of the electrodes, that a phrenic nerve of the subject was stimulated by a pacing current passed from the catheter into tissue of the subject at the particular location, and generating an output in response to the identifying.

The present invention will be more fully understood from the following detailed description of embodiments thereof, taken together with the drawings, in which:

DETAILED DESCRIPTION OF EMBODIMENTS

Overview

When performing a cardiac ablation on a subject, it is important to ensure that the phrenic nerve of the subject not be damaged. Embodiments of the present invention therefore help prevent damage to the phrenic nerve, by providing apparatus and methods for locating the phrenic nerve.

In some embodiments, for example, a catheter passes pacing currents into the subject's tissue, prior to ablating the tissue. During and/or following the passing of each such current, the impedance between one or more pairs of electrodes, which are coupled to the body of the subject, is measured. If the pacing current stimulates the phrenic nerve, the breathing of the subject will begin to quiver, thus causing the measured impedance to exhibit a characteristic quivering pattern. A processor is configured to identify this pattern, and, in response thereto, alert the physician that the phrenic nerve is near the catheter. The physician may therefore refrain from ablating the tissue, to prevent any possible damage to the phrenic nerve. Alternatively or additionally, the location at which the quivering pattern was identified may be tagged for a follow-up examination.

Advantageously, some embodiments utilize, for the above-described impedance measurements, electrodes that are also used for impedance-based navigation of the ablation catheter. In such embodiments, there may not be a need to couple additional electrodes to the subject for locating the phrenic nerve. Moreover, there is typically no need to use any additional sensors, such as accelerometers, myographic sensors, acoustic sensors, or any sensors that measure diaphragmatic compound motor action potential (CMAP) signals.

System Description

Figure 1:
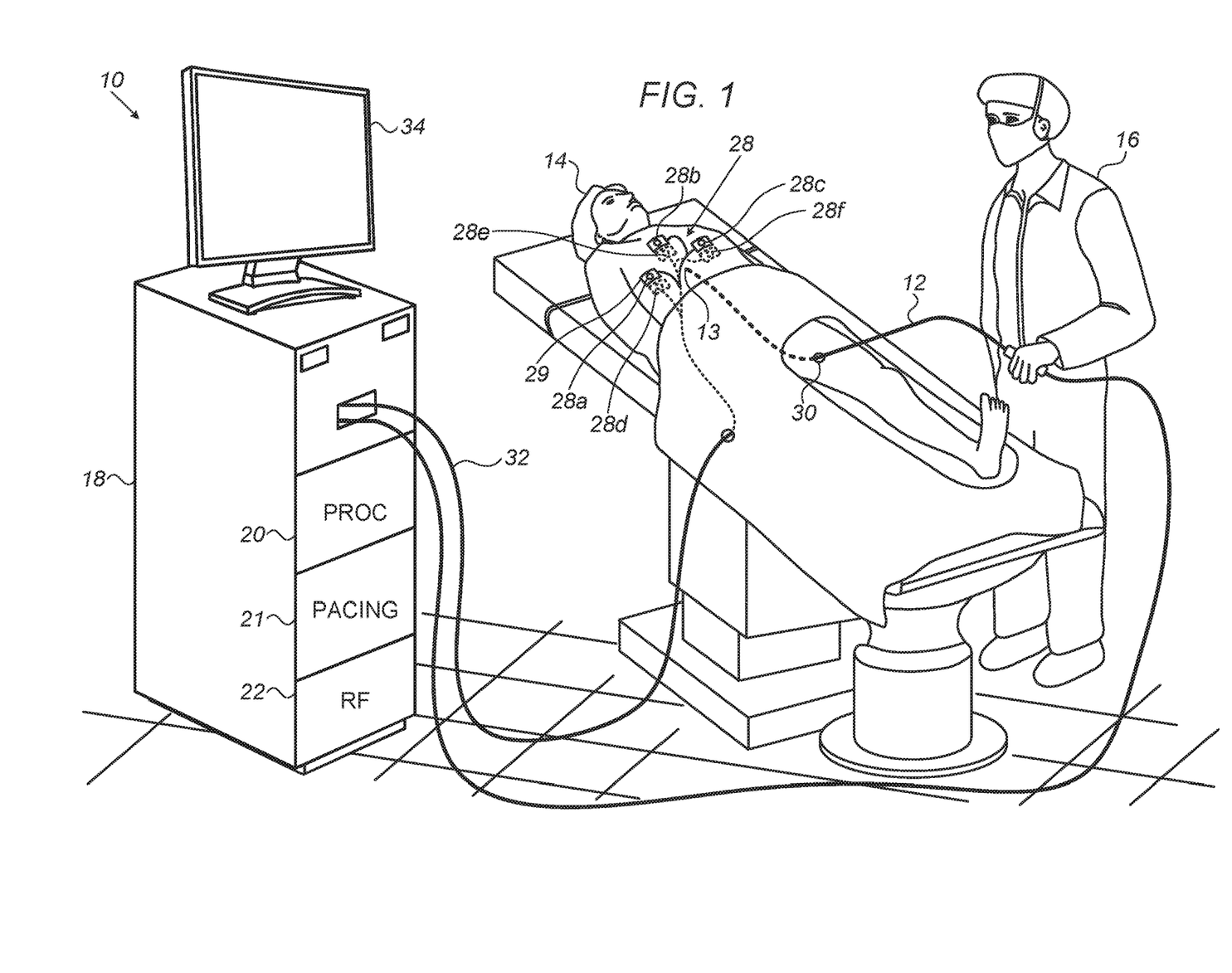
FIG. 1 is a schematic illustration of a system for ablating tissue of a subject while protecting a phrenic nerve of the subject, in accordance with some embodiments of the present invention.

Reference is initially made to FIG. 1, which is a schematic illustration of a system 10 for ablating tissue of a subject 14 while protecting a phrenic nerve of the subject, in accordance with some embodiments of the present invention.

System 10 comprises an ablation catheter 12, comprising a distal tip 13 that comprises an ablation electrode. Catheter 12 is inserted, by a physician 16, into subject 14. For example, catheter 12 may be inserted, via an insertion point 30, into vasculature of the subject, and may then be navigated, as further described below, to a particular location within the subject's heart. (In other words, distal tip 13 may be navigated to the particular location.) Subsequently, as further described below, catheter 12 is used to ascertain whether the subject's phrenic nerve is located near the particular location. If the phrenic nerve is not nearby, catheter 12 (and in particular, distal tip 13) ablates tissue of the subject at the location, by passing an ablating current into the tissue.

System 10 further comprises a plurality of electrodes 28, which are coupled to the body of subject 14. Typically, electrodes 28 are coupled to the exterior of the subject's body, e.g., via patches 29 that adhere to the skin of the subject. For example, in the particular embodiment shown in FIG. 1, system 10 comprises six electrodes, one subset of which—consisting of electrodes 28a, 28b, and 28c—are coupled to the front of the subject, and the other subset of which—consisting of electrodes 28d, 28e, and 28f—are coupled to the back of the subject. More particularly, electrodes 28a . . . c are coupled to subject's chest, while electrodes 28d . . . f are coupled to the subject's upper back, opposite the subject's chest.

Notwithstanding the above, it is noted that, in general, system 10 may comprise any suitable number of electrodes, coupled to the subject in any suitable arrangement. For example, some of the electrodes may be coupled to one side of the subject, between the subject's chest and the subject's back, with others of the electrodes coupled to the opposite side of the subject. Alternatively or additionally, some of electrodes 28 may be coupled to the interior of the subject's body.

Electrodes 28 are typically connected, via a cable 32 and an electrical interface (such as a port or socket), to a console 18, which comprises one or more units that facilitate performance of the techniques described herein. For example, console 18 may comprise a processor (PROC) 20, configured to receive information from the electrodes, and, based on this information, navigate the catheter, and also check for proximity of the catheter to the phrenic nerve. Console 18 may further comprise a pacing stimulator 21, configured to generate pacing currents, and a radiofrequency (RF) generator 22, configured to generate the RF ablation signals that are passed by catheter 12 into the subject's tissue.

Typically, system 10 further comprises a display 34, configured to facilitate performance of the procedure by displaying relevant information to physician 16. For example, processor 20 may cause display 34 to display the location of the catheter, e.g., by superimposing an icon representing the distal tip of the catheter over an image of the subject's anatomy. Alternatively or additionally, upon processor 20 ascertaining that the distal tip of the catheter is near the phrenic nerve, the processor may cause display 34 to display a suitable warning to physician 16.

As noted above, electrodes 28 are typically used to navigate the catheter within the body of the subject, using impedance-based tracking techniques, such as those described in U.S. Pat. No. 8,456,182 and US Patent Application Publication 2015/0141798, whose disclosures are incorporated herein by reference. Such techniques involve repeatedly ascertaining the location of the catheter—in particular, the distal tip thereof—responsively to the different respective impedances exhibited between the catheter and each of the electrodes, and then generating an output that indicates the ascertained location. As described above, such an output may include the display of a relevant icon on display 34, which indicates the current location of the catheter to the physician. Based on this output, the physician may steer the catheter to the desired location.

More specifically, to ascertain the location of the catheter at any given time, a current of known amplitude is passed from the distal tip of the catheter, and the resulting voltages and/or currents are measured at each of the electrodes. These voltages and currents vary between the electrodes, due to there being a different amount of electrically-impeding tissue between the distal tip of the catheter and each of the electrodes. Hence, processor 20 may derive the location of the catheter from the ratios between the measured voltages and/or currents, or between the impedances implied by these voltages and currents.

Advantageously, as noted above in the Overview, the same electrodes 28 used for navigating the catheter may also be used to ascertain whether the distal tip of the catheter is near a phrenic nerve. In some embodiments, for example, pacing currents are passed from the catheter (e.g., from the distal tip thereof, such as from the ablation electrode) into tissue (e.g., cardiac tissue) of the subject. (These currents, which are typically generated by pacing stimulator 21, are referred to as "pacing" currents, in that, when applied to the subject's heart, they pace the subject's heart.) While these currents are passed into the tissue, signals that represent the impedance between one or more pairs of electrodes are acquired, as further described below with reference to FIG. 2. From these signals, the processor ascertains whether the phrenic nerve of the subject was stimulated (and/or is currently being stimulated) by the pacing current, as described below with reference to FIG. 2. Thus, electrodes 28 serve at least two separate functions: navigation of the catheter, and identifying proximity to the phrenic nerve.

In general, processor 20 may be embodied as a single processor, or as a cooperatively networked or clustered set of processors. In some embodiments, processor 20 is implemented solely in hardware, e.g., using one or more Application-Specific Integrated Circuits (ASICs) or Field-Programmable Gate Arrays (FPGAs). In other embodiments, the processor is at least partly implemented in software. For example, processor 20 may be implemented as a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Identifying Proximity to the Phrenic Nerve

Figure 2:
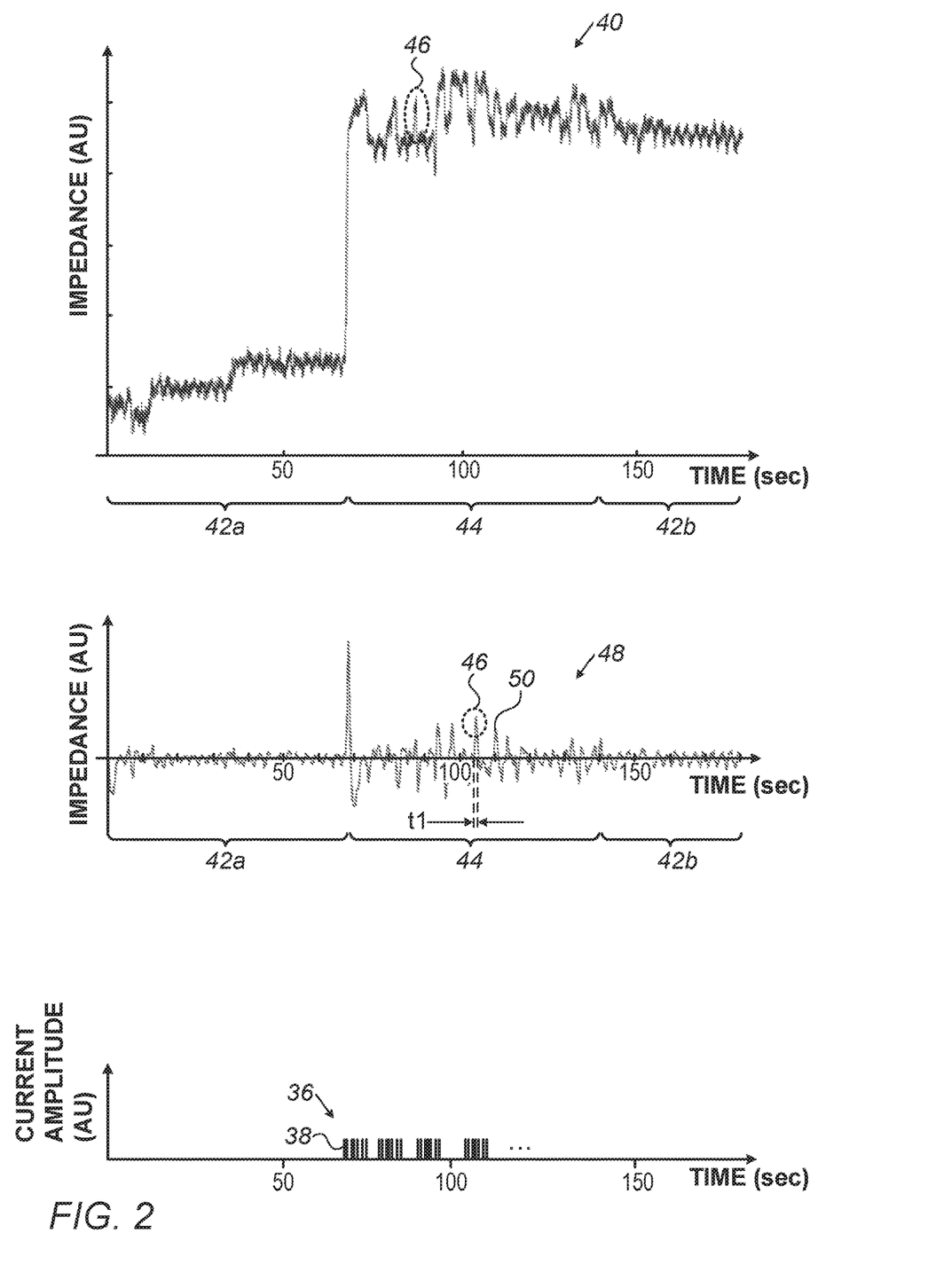
FIG. 2 is a schematic illustration of a technique for identifying proximity to a phrenic nerve, in accordance with some embodiments of the present invention.

Reference is now made to FIG. 2, which is a schematic illustration of a technique for identifying proximity to a phrenic nerve, in accordance with some embodiments of the present invention.

As described above, following the navigation of the catheter to a particular location with the body of the subject, such as a particular location within the subject's heart, the physician uses the catheter to pass pacing currents into the subject's tissue. These pacing currents typically include one or more series 36 of current-pulses 38, one such series being shown at the bottom of FIG. 2.

Typically, the magnitude of each current-pulse 38 is less than 10 mA (e.g., between 5 and 10 mA), although any other suitable magnitude, such as between 10 and 30 mA, is also within the scope of the present disclosure. Each series 36 may have any suitable duration, and successive current-pulses 38 may be spaced apart from one another by any suitable time interval. For example, each series 36 may have a duration of several seconds (e.g., 5-10 seconds), with successive current-pulses 38 in the series being spaced apart from one another by an interval of 200-600 ms, such as 200-300 ms. Successive series 36 may be spaced apart from one another by any suitable interval, such as 0.5-3 seconds. As illustrated in FIG. 2, the time interval that separates between successive current-pulses in series 36, and the time interval that separates between successive series 36, are not necessarily constant throughout the procedure.

FIG. 2 (top) also shows an impedance signal 40, which represents an impedance measured between a pair of electrodes 28. Such a pair of electrodes typically includes a first electrode that is coupled to the front of the subject, and a second electrode that is coupled to the back of the subject. In general, the impedance between such a pair of electrodes varies as a function of the amount of air in the lungs of the subject, as well as the distance between the electrodes, which changes over the respiratory cycle of the subject. In particular, as the subject inhales, the impedance between the electrodes increases, due to the increased amount of air between the electrodes, and the increased distance between the electrodes; conversely, as the subject exhales, the impedance between the electrodes decreases.

FIG. 2 illustrates a scenario in which the distal tip of the catheter is near the phrenic nerve, such that at least some of current-pulses 38 stimulate the phrenic nerve. Due to stimulation of the phrenic nerve, impedance signal 40 includes three distinctive portions, acquired during different respective time intervals: a first normal-respiration portion 42a, obtained prior to the application of current-pulses 38, a second normal-respiration portion 42b, obtained following the application of current-pulses 38, and an abnormal-respiration portion 44, obtained during the application of current-pulses 38. Abnormal-respiration portion 44 includes a plurality of spikes 46, which appear in the signal at the approximate times at which current-pulses 38 are applied. (A large initial spike 46 may be observed at the start of abnormal-respiration portion 44, at the time of the first applied current-pulse.) Each of spikes 46 indicates a respirational quiver, caused by stimulation of the phrenic nerve. In particular, stimulation of the phrenic nerve causes a small amount of air to be rapidly inhaled, causing a small, rapid increase in impedance, and then rapidly exhaled, causing a small, rapid decrease in impedance. Abnormal-respiration portion 44 may therefore be said to exhibit a quivering pattern, marked by a succession of spikes 46. In some embodiments of the present invention, processor 20 identifies that the phrenic nerve of the subject was stimulated, by identifying this quivering pattern.

Typically, the processor does not directly search impedance signal 40 for the quivering pattern. Rather, the processor first preprocesses impedance signal 40, such as to yield a preprocessed impedance signal 48, shown in the middle of FIG. 2, and then searches preprocessed impedance signal 48 for the quivering pattern. For example, preprocessed impedance signal 48 may be a filtered version of impedance signal 40, obtained by applying a bandpass filter to impedance signal 40. (Such a filter may, for example, filter out frequencies that are less than 0.2 Hz or greater than 1 Hz.) The removal of low frequencies helps remove slow changes in the signal resulting from normal respiration, such that preprocessed impedance signal 48 oscillates around a baseline value of zero. The removal of high frequencies helps remove noise from the signal.

Following the computation of preprocessed impedance signal 48, the processor identifies the quivering pattern in this signal. In some embodiments, the quivering pattern is identified by identifying a longer amount of time t1 between successive zero crossings of abnormal-respiration portion 44 of preprocessed impedance signal 48, relative to the other portions of preprocessed impedance signal 48. Alternatively or additionally, the processor may identify the quivering pattern by identifying a larger amplitude of peaks 50 of abnormal-respiration portion 44, relative to other portions of the signal.

In some embodiments, the processor further computes the frequency of the identified quivering pattern, and checks if this frequency corresponds to (i.e., is within a given offset of) the frequency at which the pacing current was passed into the tissue. If the processor identifies such a correspondence, the processor may identify, with greater confidence, that the phrenic nerve was stimulated. For example, if current-pulses 38 were applied at a particular frequency (e.g., 333 Hz, corresponding to a spacing of 300 ms between successive current-pulses), the processor may check that the zero crossings that precede the larger-amplitude peaks 50 occur at approximately the same frequency. Alternatively or additionally, if multiple series 36 of current-pulses were applied, the processor may check that the quivering pattern occurs in those portions of the signal corresponding to the time periods during which series 36 were applied, but not during the "quiet" time periods between successive series.

In some embodiments, the pacing current is passed into the tissue during a plurality of time periods and with a plurality of different respective pacing frequencies. For example, the frequency of current-pulses 38 may be varied across multiple series 36 of current-pulses, and/or the frequency with which series 36 are passed into the tissue may be varied across multiple time periods. The processor may then identify stimulation of the phrenic nerve by identifying that the frequency of the quivering, during each of the time periods, corresponds to (i.e., is within a given offset of) the pacing frequency with which the pacing current was passed into the tissue during the time period.

For example, during a first time period, a first series 36 of current-pulses, having a frequency of 333 Hz, may be passed into the tissue. Next, during a second time period, a second series 36 of current-pulses, having a frequency of 500 Hz (corresponding to a spacing of 200 ms between successive current-pulses), may be passed into the tissue. The processor may then confirm that the phrenic nerve was stimulated, by identifying a quivering frequency of approximately 333 Hz during the first time period, and a quivering frequency of approximately 500 Hz during the second time period.

In the example shown in FIG. 2, the values obtained by impedance signal 40 and preprocessed impedance signal 48 are actual impedance values (stated in units of Ohms, for example). It is noted, however, that in the context of the present description and claims, a signal having voltage or current values may also represent an impedance between a pair of electrodes, such that signals 40 and 48 may alternatively have voltage or current values. (Since, however, current is inversely proportional to impedance, a current signal will quiver inversely to the manner described above, in the sense that each spike 46 will include a small, rapid drop, followed by a small, rapid increase.)

Typically, during and/or after the application of the pacing currents, the processor iterates over the respective impedance signals measured (as described below) between multiple pairs of electrodes 28, and attempts to identify a quivering pattern in each of these signals. If a quivering pattern is identified in at least one the signals, the processor identifies that the phrenic nerve was stimulated, and, in response thereto, generates an output on display 34 (FIG. 1), such as a warning indicating that an ablation should not be performed at the catheter's present location. Alternatively or additionally, the processor may generate any other type of output, such as an audio output, indicating that the phrenic nerve was stimulated.

For example, with reference to the configuration of electrodes shown in FIG. 1, the processor may check each impedance measured between a pair of opposite external electrodes. That is, the processor may check the impedance between (i) a first pair of electrodes 28a and 28d, (ii) a second pair of electrodes 28b and 28e, and (iii) a third pair of electrodes 28c and 28f. Alternatively, the processor may iterate over the nine (3×3) impedances between front electrodes 28a, 28b, and 28c and back electrodes 28d, 28e, and 28f. Alternatively, the processor may iterate over the 15 ((6×5)/2) impedances between the 15 pairs of external electrodes. If any of these signals indicates stimulation of the phrenic nerve, the processor may generate an appropriate output.

Measurement of Impedances

It is noted that the impedance between a given pair of external electrodes may be measured under two different sets of conditions:

(i) One set of conditions is where any current passed from a given external electrode 28i is distributed among all of the other external electrodes. The impedance measured between external electrode 28i and another external electrode 28j under this set of conditions will be indicated by the notation $Z_{ij}$. For example, $Z_{ab}$ indicates the impedance measured between electrodes 28a and 28b when a current from electrode 28a flows to all of electrodes 28b . . . f.

(ii) Another set of conditions is where any current passed from a given external electrode 28i flows to only one other external electrode 28j. The impedance measured between external electrodes 28i and 28j under this set of conditions will be denoted by the notation $Q_{ij}$. For example, $Q_{ab}$ indicates the impedance measured between electrodes 28a and 28b when a current from electrode 28a flows entirely to electrode 28b.

In some embodiments, impedances $Z_{ij}$ are used for signals 40. In such embodiments, the processor causes (e.g., by sending appropriate control signals to the electrodes) respective electric currents to be passed between different pairs of the electrodes, at least while the pacing current is passed into the tissue. These currents, which may be passed at the same time at different respective frequencies, are used to measure the respective impedances $Z_{ij}$. The processor may then check any of these signals (e.g., after appropriate preprocessing) for a quivering pattern, as described above.

For example, to measure the impedances $Z_{ab}$, $Z_{ac}$, etc., the processor may cause an electric current to be passed from electrode 28a, and then receive, from respective voltmeters and ammeters at electrodes 28b . . . f, the respective voltages and currents measured at these electrodes. The processor may then derive the impedances from these measurements; for example, to derive $Z_{ab}$, the processor may divide the voltage measured at electrode 28b (relative to that of electrode 28a) by the current measured at electrode 28b. Similarly, to measure the impedances $Z_{ba}$, $Z_{bc}$, etc., the processor may cause an electric current to be passed from electrode 28b, and then derive the impedances from the resulting voltages and currents measured at electrodes 28a and 28c . . . f.

In other embodiments, impedances $Q_{ij}$ are used for signals 40. Typically, in such embodiments, impedances $Q_{ij}$ are not measured directly under the second set of conditions; rather, impedances $Q_{ij}$ are derived from impedances $Z_{ij}$, which may be measured under the first set of conditions as described above. For example, impedances $Q_{ij}$ may be calculated by the following technique:

(i) Measure $Z_{ij}$ for each pair of electrodes 28i and 28j.
(ii) Define an N×N matrix S with elements $$S_{ij} = \begin{cases} -1/Z_{ij} & i \neq j \\ \sum_{k=1, k \neq i}^{N} 1/Z_{ik} & i = j \end{cases},$$

where N is the total number of electrodes.

(iii) Calculate R, the Moore-Penrose pseudo-inverse of S.
(iv) Calculate each impedance $Q_{ij}$ according to the formula $Q_{ij} = R_{ii} + R_{jj} - R_{ij} - R_{ji}$.

Although the present disclosure relates to locating the phrenic nerve mainly in the context of cardiac ablations, it is noted that the techniques described herein may be used to locate the phrenic nerve in any relevant context. For example, in some cases, a physician may wish to locate the phrenic nerve of a subject before injecting a substance (such as an anesthetic) into the subject, in order to help prevent unintended injury to the phrenic nerve.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for ablating a subjects tissue while protecting a phrenic nerve of the subject, said system comprising:
   a catheter comprising a distal tip having an ablation electrode, the distal tip movable within the subject's body;
   a pacing stimulator configured to generate pacing currents from the catheter;
   a radiofrequency generator configured to generate radio frequency ablation signals that are passed by the catheter into the subject's tissue;
   a plurality of other electrodes other than the ablation electrode, said other electrodes configured to be electrically coupled to the body of the subject; and
   a processor configured to:
      navigate the catheter within the body of the subject to a particular location by ascertaining the current location of the catheter in response to the different respective impedances exhibited between the catheter and each of the other electrodes,
      ascertain whether the distal tip of the catheter is near the phrenic nerve of the subject at the particular location when pacing current is passed from the catheter into the subject's tissue by detecting whether the phrenic nerve of the subject is stimulated by the pacing current,
      acquire impedance signals that represent the impedance between one or more pairs of the other electrodes when such pacing current is passed from the catheter into the subject's tissue, and
      determine whether the phrenic nerve of the subject was stimulated by the pacing current based on the impedance signals; wherein the impedance signals which determine whether the phrenic nerve of the subject was stimulated by the pacing current are effective to indicate whether damage to the phrenic nerve may result if ablating of the subject's tissue at the current location of the catheter is performed.

2. The system according to claim 1, wherein the processor is configured to acquire the impedance signal by causing an electric current to be passed between a given pair of the other electrodes while the pacing current is passed into the tissue.

3. The system according to claim 2, wherein the processor is configured to acquire the impedance signal by:
   causing respective electric currents to be passed between a plurality of pairs of the other electrodes, including the given pair of the other electrodes, while the pacing current is passed into the tissue, and
   deriving the impedance signal from respective impedances measured between the pairs of the other electrodes while the electric currents are passed.

4. The system according to claim 1, wherein an output of said system includes a warning indicating that the tissue at the particular location should not be ablated.

5. The system according to claim 1,
   wherein some of the other electrodes are configured to be coupled to a front of the subject and others of the other electrodes are configured to be coupled to a back of the subject, and
   wherein a given pair of the other electrodes includes one of the other electrodes coupled to the front of the subject and one of the other electrodes coupled to the back of the subject.

6. The system according to claim 1, wherein the processor is configured to navigate the catheter by repeatedly:
   ascertaining the current location of the catheter, responsive to different respective impedances exhibited between the catheter and each of the other electrodes, and
   generating an output that indicates the ascertained location.

7. The system according to claim 1, wherein the processor is configured to identify a quivering pattern by identifying a longer amount of time between successive zero-crossings of a first portion of the impedance signal, relative to other portions of the impedance signal.

8. The system according to claim 1, wherein the processor is configured to identify a quivering pattern by identifying a larger amplitude of peaks of a first portion of the impedance signal, relative to other portions of the impedance signal.

9. The system according to claim 1,
   wherein the pacing current is passed into the tissue during a plurality of time periods, and
   wherein the processor is configured to identify that the phrenic nerve was stimulated by identifying a quivering pattern in those portions of the impedance signal corresponding to the time periods, but not in other portions of the impedance signal.

10. A method for ablating a subject's tissue while protecting a phrenic nerve of the subject, said method comprising:
    providing a catheter comprising a distal tip having an ablation electrode, the distal tip movable within the subject's body;
    providing a pacing stimulator configured to generate pacing currents from the catheter;
    providing a radiofrequency generator configured to generate radio frequency ablation signals that are passed by the catheter into the subject's tissue;
    providing a plurality of other electrodes other than the ablation electrode which are coupled to the body of the subject;
    navigating the catheter within the body of the subject to a particular location of the catheter in response to the different impedance exhibited between the catheter and each of the other electrodes;
    passing a pacing current from the catheter into the subject's tissue;
    ascertaining whether the distal tip of the catheter is near the phrenic nerve of the subject when the pacing current is passed from the catheter into the subject's tissue at the particular location by detecting whether the phrenic nerve of the subject is stimulated by the pacing current;
    acquiring impedance signals that represent the impedance between one or more pairs of the other electrodes;
    determining from said impedance signals whether the phrenic nerve of the subject was stimulated by the pacing current; and if so, generating an audio output and/or an output on a display to indicate that the phrenic nerve of the subject was stimulated by the pacing current;

wherein the impedance signals which determine whether the phrenic nerve of the subject was stimulated by the pacing current are effective to indicate whether damage to the phrenic nerve may result if ablating of the subject's tissue at the current location of the catheter is performed.

11. The method according to claim 10, wherein acquiring the impedance signals comprises causing an electric current to be passed between a given pair of the other electrodes at least while the pacing current is passed into the tissue.

12. The method according to claim 11, wherein acquiring the impedance signals comprises:

causing respective electric currents to be passed between a plurality of pairs of the other electrodes, including the given pair of the other electrodes, at least while the pacing current is passed into the tissue, measuring respective impedances between the pairs of the other electrodes while the electric currents are passed, and deriving the impedance signals from the respective impedances.

13. The method according to claim 10, wherein generating an output comprises displaying a warning indicating that the tissue at the particular location should not be ablated.

14. The method according to claim 10, wherein some of the other electrodes are coupled to a front of the subject and some of the other electrodes are coupled to a back of the subject, and wherein the pair of the other electrodes includes one of the other electrodes coupled to the front of the subject and one of the other electrodes coupled to the back of the subject.

15. The method according to claim 10, wherein navigating the catheter comprises repeatedly:

ascertaining the current location of the catheter, responsive to different respective impedances exhibited between the catheter and each of the other electrodes, and generating an output that indicates the ascertained location.

16. The method according to claim 10, further comprising identifying a quivering pattern in the impedance signal by identifying a longer amount of time between successive zero-crossings of a first portion of the impedance signal, relative to other portions of the impedance signal.

17. The method according to claim 10, further comprising identifying a quivering pattern in the impedance signal by identifying a larger amplitude of peaks of a first portion of the impedance signal, relative to other portions of the impedance signal.

18. The method according to claim 10, wherein the pacing current is passed into the tissue during a plurality of time periods, and wherein identifying that the phrenic nerve was stimulated comprises identifying a quivering pattern in those portions of the impedance signal corresponding to the time periods, but not in other portions of the impedance signal.

* * * * *